United States Patent
Haartsen et al.

(10) Patent No.: US 9,987,462 B2
(45) Date of Patent: Jun. 5, 2018

(54) ELONGATED INTERVENTIONAL DEVICE WITH VARIABLE STIFFNESS

(71) Applicant: KONINKLIJKE PHILIPS N.V., Eindhoven (NL)

(72) Inventors: Jacob Roger Haartsen, Eindhoven (NL); Martinus Bernardus Van Der Mark, Eindhoven (NL); Franciscus Johannes Gerardus Hakkens, Eindhoven (NL); Maurice Hubertus Elisabeth Van Der Beek, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days. days.

(21) Appl. No.: 15/318,730

(22) PCT Filed: Jun. 1, 2015

(86) PCT No.: PCT/EP2015/062104
§ 371 (c)(1),
(2) Date: Dec. 14, 2016

(87) PCT Pub. No.: WO2015/193089
PCT Pub. Date: Dec. 23, 2015

(65) Prior Publication Data
US 2017/0119998 A1 May 4, 2017

(30) Foreign Application Priority Data
Jun. 18, 2014 (EP) .................................. 14172894

(51) Int. Cl.
*G02B 6/00* (2006.01)
*A61M 25/00* (2006.01)
(Continued)

(52) U.S. Cl.
CPC .......... *A61M 25/0043* (2013.01); *A61F 2/95* (2013.01); *A61M 25/09041* (2013.01); *A61M 2025/0064* (2013.01); *A61M 2025/09158* (2013.01)

(58) Field of Classification Search
CPC ............ G02B 6/02057; G02B 6/02076; G02B 6/02085; A61M 25/0043;
(Continued)

(56) References Cited

U.S. PATENT DOCUMENTS 4,543,090 A * 9/1985 McCoy ............ A61M 25/0158
600/151
4,934,340 A * 6/1990 Ebling ................ A61B 1/0058
600/117

(Continued)

FOREIGN PATENT DOCUMENTS

| EP | 1418971 B1 | 5/2007 |
| WO | 2004032746 A2 | 4/2004 |
| WO | 2013116096 A1 | 8/2013 |

OTHER PUBLICATIONS

Erdogan, T. et al "Tilted Fiber Phase Gratings", Journal Optical Society of America, vol. 13, No. 2, Feb. 1996.
(Continued)

*Primary Examiner* — Rhonda Peace (57) ABSTRACT

An elongated device includes an optical fiber arranged to allow transmission of light to phase change material arranged long the elongated device, for optically heating the phase change material to change its stiffness from one stiffness value to a different stiffness value. Using distributed tilted or blazed Bragg gratings with light wavelength dependent unique grating periods along the optical fiber, a guide wire or catheter is provided which can be stiffness controlled at selected longitudinal portions. Behavior of the tip of a guide wire or catheter is controlled for optimal navigation.

(Continued)

Portions of phase change material arranged inside a tube material can be activated at selected longitudinal parts of the elongated device.

11 Claims, 4 Drawing Sheets (51) Int. Cl.
*A61M 25/09* (2006.01)
*A61F 2/95* (2013.01)

(58) Field of Classification Search
CPC .... A61M 25/09041; A61M 2025/0064; A61M 2025/09141; A61F 2/95
See application file for complete search history.

(56) References Cited

U.S. PATENT DOCUMENTS

| | | | | |
|---|---|---|---|---|
| 5,334,168 | A * | 8/1994 | Hemmer | A61M 25/0158 604/531 |
| 5,531,685 | A * | 7/1996 | Hemmer | A61M 25/0158 604/531 |
| 5,662,621 | A | 9/1997 | Lafontaine | |
| 5,846,247 | A * | 12/1998 | Unsworth | A61F 2/88 606/108 |
| 6,468,203 | B2 * | 10/2002 | Belson | A61B 1/0053 600/145 |
| 6,522,810 | B2 * | 2/2003 | Takushima | G02B 6/02095 385/27 |
| 6,533,752 | B1 * | 3/2003 | Waram | A61B 1/0058 604/530 |
| 7,018,346 | B2 * | 3/2006 | Griffin | A61M 25/09 600/585 |
| 7,389,022 | B2 | 6/2008 | De Barros | |
| 7,526,156 | B2 * | 4/2009 | Lee | G02B 6/4203 385/15 |
| 7,559,916 | B2 | 7/2009 | Smith | |
| 7,828,790 | B2 * | 11/2010 | Griffin | A61M 25/005 604/525 |
| 8,328,791 | B2 * | 12/2012 | Griffin | A61M 25/005 604/525 |
| 8,649,847 | B1 | 2/2014 | Park | |
| 9,164,084 | B2 * | 10/2015 | Cheng | A61B 5/0073 |
| 9,417,057 | B2 * | 8/2016 | 'T Hooft | G01B 11/16 |
| 2002/0013550 | A1 | 1/2002 | Unsworth | |
| 2004/0106898 | A1 | 6/2004 | Masunishi | |
| 2006/0069346 | A1 | 3/2006 | Smith | |
| 2008/0019657 | A1 | 1/2008 | Maitland | |
| 2008/0089644 | A1 | 4/2008 | Lee | |
| 2013/0158512 | A1 * | 6/2013 | Gutierrez | A61M 25/09041 604/510 |
| 2015/0141764 | A1 * | 5/2015 | Harks | A61B 5/0084 600/301 |
| 2015/0282693 | A1 | 10/2015 | Hakkens | |
| 2017/0119998 | A1 * | 5/2017 | Haartsen | A61M 25/0043 |

OTHER PUBLICATIONS

Ryu, Seok Chang et al "Feasibility Study of an Optically Actuated MR-Compatible Active Needle", Intelligent Robots and Systems, 2013.

Caucheteur, C. et al "Simultaneous bend and temperature sensor using tilted FBG", Proceedings of SPIE, 2005.

Caucheteur, C. et al, "Light Polarization-Assisted Sensing with Tilted Fiber Bragg Gratings", The Open Optics Journal, vol. 7, pp. 95-103, 2013.

Erdogan, T. et al "Radiation-Mode Coupling Loss in Tilted Fiber Phase Gratings", Optics Letters, vol. 20, Issue 18, 1995—Abstract Only.

* cited by examiner

ELONGATED INTERVENTIONAL DEVICE WITH VARIABLE STIFFNESS

CROSS-REFERENCE TO PRIOR APPLICATIONS

This application is the U.S. National Phase application under 35 U.S.C. § 371 of International Application No. PCT/EP2015/062104, filed on Jun. 1, 2015, which claims the benefit of European Patent Application No. 14172894.9, filed on Jun. 18, 2014. These applications are hereby incorporated by reference herein.

FIELD OF THE INVENTION

The present invention relates to the field of medical devices. More specifically, the invention provides an elongated interventional device with variable stiffness, e.g. in the form of a guide wire or catheter with a variable stiffness of its tip.

BACKGROUND OF THE INVENTION

Catheterization has become one of the most widely used procedures in cardiovascular analysis and treatment. For example in abdominal aneurism repair a stent is placed in an aneurism, which is a weakened part of the abdominal aorta, to prevent further widening and ultimately rupture of the aneurism.

In the case of a so-called Fenestrated EndoVascular Abdominal aneurism Repair (FEVAR) procedure, the renal arteries need to be stented as well. Here, a combination of catheters and guide wires is used to bring the stent into position: First a soft guide wire with a pre-formed tip and a catheter are used to navigate to the renal arteries. In this step often several guide wires, each with a different stiffness, are tried before the surgeon succeeds in positioning the tip of the guide wire and catheter in the renal artery. After this step, while keeping the catheter in position, the soft guide wire is removed and a stiff guide wire is introduced. When the stiff guide wire is in place, the catheter is removed and a catheter with the stent is railed over the stiff guide wire in order to position the stent in the renal artery. Hereby it is essential that the guide wire is sufficiently stiff in order to be able to guide the catheter with the stent.

US 2002/0013550 A1 discloses an apparatus having a steerable distal end portion for insertion in the body lumen which comprises a superelastic shape memory member. Heating the superelastic shape memory member inside the body lumen caused it to increase in stiffness and tend toward a memorized shape, and subsequent discontinuation of heating causes the superelastic shape memory member to decrease in stiffness.

WO 2013/116096 A1 discloses methods for determining aggressiveness of a cancer and treatment thereof. An apparatus used in these methods comprises a light source and at least one optical fiber for transmitting the light. For redirecting the light onto tissue, the optical fiber has a blazed fiber Bragg grating with obliquely impressed index changes that are at a non-perpendicular angle to the longitudinal axis of the optical fiber.

U.S. Pat. No. 5,662,621 discloses a guide catheter, wherein the catheter shaft can be changed between a generally ductile state and a relatively stiff state through exposure to light. The ultraviolet or laserlight rays change the guide catheter from a relatively stiff state to a softened, ductile state.

US 2008/0019657 A1 discloses a system for diffusing light from an optical fiber coupled to a light source, comprising a polymer element adapted to be connected to the optical fiber and having incorporated a scattering element, wherein the scattering element diffuses the light.

US 2004/0106898 A1 discloses a photothermal actuator comprising an optical fiber bundle, a light inputting apparatus, and a thermal receiving element. The thermal receiving element is provided on the part of an outer surface of the optical fiber bundle. The thermal receiving element is heated by absorption of the light so that the thermal receiving element and the part of the optical fiber bundle are stretched, whereby the optical fiber bundle and a tube, in which the optical fiber bundle is inserted, are bent.

SUMMARY OF THE INVENTION

Following the above, it would be advantageous to reduce the amount of steps needed to bring the stent in place, e.g. in a FEVAR procedure, so as to speed up the procedure to reduce the patient's exposure to harmful X-rays and contrast agents, and e.g. reduce the risk of errors during the procedure.

In a first aspect, the invention provides an elongated device comprising:

a phase change material arranged along at least a part of a longitudinal extension of the elongated device, and an optical fiber arranged in relation to the phase change material so as to allow transmission of light from a proximal end of the optical fiber to at least part of the phase change material for optically providing heat to said at least part of the phase change material to cause said at least part of the phase change material to change its stiffness from one stiffness value to a different stiffness value, wherein the optical fiber comprises a plurality of longitudinal portions with tilted or blazed gratings arranged for guiding light in a direction away from the longitudinal extension of the optical fiber at respective longitudinal portions of the optical fiber, wherein a tilt angle of the gratings is selected so as to guide light of a specific range of wavelengths evenly along at least a longitudinal portion of the optical fiber.

Such elongated device is advantageous, e.g. in the form of a guide wire or catheter that can be used e.g. in FEVAR procedures to eliminate the need for several catheters or guide wires to be used during such procedure. It is possible to have a guide wire or catheter which is capable of changing its stiffness and thus adapt its properties from soft to stiff in a controlled manner during the FEVAR procedure, e.g. by controlling stiffness independently of several longitudinal segments of the guide wire or catheter, especially of the tip region of the guide wire or catheter. This allows the steps of positioning the guide wire or catheter tip and the subsequent step of railing a stent in position to be performed with one single guide wire or catheter. Thus, the number of procedural steps during a FEVAR procedure can be reduced. Furthermore, with such FEVAR procedure, the patient's exposure to harmful X-rays and contrast agents during the procedure can be reduced.

Yet further, by using light to control a change in stiffness of the phase change material transmitted by the involved optical fiber(s), the procedure is MR compatible since the guide wire or catheter can be manufactured without the need for magnetic materials.

The optical fiber comprises a plurality of longitudinal portions with tilted or blazed gratings arranged for guiding light in a direction away from the longitudinal extension of the optical fiber at respective longitudinal portions of the optical fiber. Especially, the gratings at said plurality of longitudinal portions of the optical fiber may have respective unique grating periods, so as to allow light wavelength dependent activation of phase change material arranged at said plurality of longitudinal portions. Especially, a tilt angle of the gratings is selected so as to guide light of a specific range of wavelengths evenly along at least a longitudinal portion of the optical fiber, differently from WO 2013/116096 A1, which teaches a particular combination of blaze angle of the grating and wavelength so that the light is redirected perpendicular to the longitudinal axis of the optical fiber.

The tilted gratings preferably comprise Bragg gratings.

In the following, a number of optional additional features and/or embodiments will be defined.

Preferably, the optical fiber is arranged to transmit light from a proximal end of the optical fiber for providing heat to a plurality of different portions of phase change material arranged at different longitudinal positions of the elongated device. Especially, it is preferred that these different longitudinal portions can be selected in response to the light applied to the proximal end of the optical fiber. This allows controlling stiffness of different longitudinal segments of a guide wire or catheter, and thus allows an improved way of navigating such guide wire or catheter. Especially, this may be implemented with separate optical fiber cores arranged for transmitting light to respective longitudinal portions of the phase change material arranged along the elongated device. However, one single optical fiber core may be used to do so, which will be elucidated in the following.

The tilted or blazed gratings at said plurality of longitudinal portions of the optical fiber may be arranged to guide light in a direction away from the longitudinal extension of the optical fiber at respective different wavelengths of light. More specifically, the phase change material may be arranged at least along said longitudinal portions of the optical fiber, so as to allow wavelength dependent change of stiffness of different longitudinal portions of the elongated device.

The elongated device may comprise an elongated tube containing said phase change material at least at a part of its longitudinal extension, wherein the optical fiber is arranged inside said elongated tube. Especially, the elongated tube may be formed by a thermally conducting material, and wherein portions of phase change material is arranged within the thermally conducting material. Such thermally conducting material may comprise the material Pebax® or e.g. Pebax® filled with thermal conductive ceramic or metal particles for increased thermal conductivity.

The phase change material may be selected such that it increases its stiffness in response to application of heat, which allows e.g. FEVAR procedure, where the elongated device is preferably relatively soft in the beginning of the procedure, while it is preferred that at least a part of the elongated device is stiffened to allow railing of a stent into position. The phase change material should at least have a melting point above body temperature and may comprise at least one of: paraffins (e.g. N-henicosan, tristearin), fatty acids (e.g. lauric acid) or salt hydrates. Such materials are known in the art. It is preferred, that the method is arranged to increase stiffness by a factor of such as 50 in response to heat applied by light. The light applied may be in the light wavelength range of such as 400-2000 nm.

Preferably, at least a part of the phase change material is arranged along a distal end portion of the elongated device. Hereby, at least a part of the tip of a guide wire or catheter can be controlled with respect to stiffness, thus providing improved navigation properties for a user. It may be preferred that the optical fiber is arranged to allow a plurality of different longitudinal portions of the distal end portion of the elongated device to be optically controlled.

The optical fiber may comprise a plurality of optical fiber cores arranged within one common cladding. Especially, at least one of said plurality of optical fiber cores is arranged to provide light to phase change material arranged outside said cladding. Especially, at least one of said plurality of optical fiber cores comprises optical elements is arranged for optical shape sensing. Especially, at least one of the plurality of optical fiber cores arranged within said common cladding is arranged for optical shape sensing, i.e. said at least one optical fiber core has optical element allowing optical interrogation to allow reconstruction of its shape.

The elongated device may be in the form of an interventional guide wire or an interventional catheter.

In a second aspect, the invention provides a system comprising:

an elongated device according to the first aspect, and a light source arranged for connection to the proximal end of optical fiber for providing light to cause said at least part of the phase change material to change its stiffness from one stiffness value to a different stiffness value. Especially, the light source is arranged for selection between a plurality of different modes of operations, wherein the light source provides light with different wavelengths in said different modes of operations, and wherein the optical fiber of the elongated device is arranged to guide light away from a longitudinal extension at respective different longitudinal positions in response thereto.

In a third aspect, the invention provides a method for controlling an elongated device, the method comprising:

providing an elongated device according to the first aspect comprising an optical fiber arranged to transmit light from its proximal end to a phase change material arranged along at least a longitudinal portion of the elongated device, and providing light to a proximal end of the optical fiber, so as to optically provide heat to said portion of the phase change material to cause said portion of the phase change material to change its stiffness from one stiffness value to a different stiffness value. Especially, the method may comprise selecting between a plurality of different wavelengths of light, so as to select where, between a plurality of different longitudinal portions of the elongated device, to guide light into the phase change material, especially the optical fiber comprises a plurality of longitudinal portions with different wavelength dependent tilted Bragg gratings.

In a fourth aspect, the invention provides a FEVAR procedure comprising:

providing an interventional catheter or guide wire comprising an elongated device according to the first aspect, positioning a tip of the interventional catheter or guide wire in an artery, applying light to a proximal end of the optical fiber so as to provide a stiffening of at least a longitudinal portion of the catheter or guide wire, and railing a stent over the catheter or guide wire after said stiffening, so as to position the stent in the artery. In case of a phase change material that softens when heat is applied, the procedure may be to apply heat, i.e. light, during position of the tip, and then to stop or at least reduce applying light in order to stiffen the tip.

It is appreciated that the same advantages and embodiments of the first aspect apply as well for the second and third aspect. In general the first, second, third, and fourth aspects may be combined and coupled in any way possible within the scope of the invention. These and other aspects, features and/or advantages of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 1:
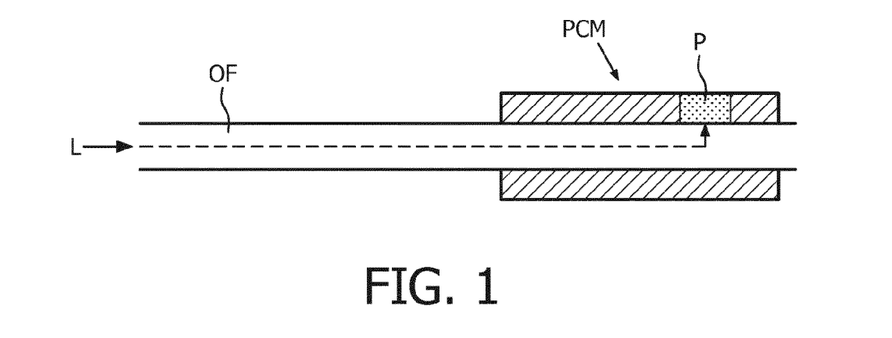
FIG. 1 illustrates a simple sketch of an embodiment.

FIG. 1 illustrates a simple sketch of basic parts of an embodiment, e.g. parts of a medical guide wire or catheter. A portion of phase change material PCM is arranged along a part of a longitudinal extension of the elongated device, here illustrated as the distal end portion of the elongated device. An optical fiber OF is arranged to guide light to the phase change material PCM so as to allow transmission of light L from a proximal end of the optical fiber OF to at least part P of the phase change material PCM for optically providing heat to this part P of the phase change material PCM. Hereby, this part P of the phase change material PCM will change its stiffness from one stiffness value to a different stiffness value, e.g. from "soft" to "hard", or the opposite way. This allows control of the behavior of the elongated device, which is advantageous e.g. for navigating a guide wire or catheter in an interventional medical procedure, such as a FEVAR procedure. It is to be understood that the light source providing the light L and the phase change material PCM should be matched to allow enough optical heat to be transmitted to the phase change material PCM to make it change from one phase to another phase.

In the illustration of FIG. 1, light L is guided longitudinally in the optical fiber OF until it reaches an optical element which guides the light L out of the optical fiber OF an into the phase change material PCM that surrounds the optical fiber OF. This can be obtained by gratings. Especially, it is preferred that the optical fiber OF comprises optical elements arranged at respective longitudinal positions, so as to enable independent control of multiple segments of the catheter with the use of a single optical fiber OF. Hereby, an increased navigation of the elongated device can be obtained.

Figure 2:
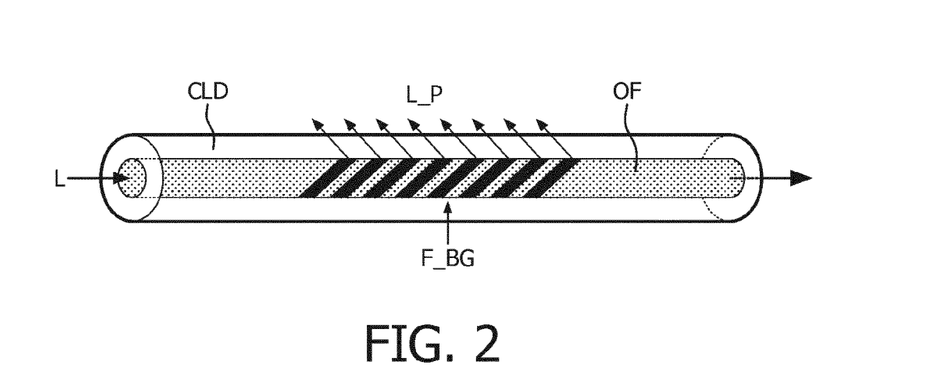
FIG. 2 illustrates a sketch of another embodiment.

FIG. 2 illustrates another sketch of an optical fiber OF into which light L is applied to one end. By means of tilted or blazed Bragg gratings F_BG, a portion of the light L_P is guided out of the optical fiber, i.e. in a direction away from a longitudinal extension of the optical fiber OF, e.g. perpendicular to the longitudinal extension of the optical fiber OF. Similar to reflection of light with a wavelength matching the Bragg condition in a conventional Bragg grating, light which otherwise would be reflected in the fiber core is partly or fully coupled into the cladding CLD (guided cladding modes) and partly into radiation modes, and hence is coupled out of the optical fiber OF. This allows control of the longitudinal position where light is guided out of the optical fiber OF and thus into surrounding or adjacently positioned phase change material (not shown in FIG. 2).

Figure 3:
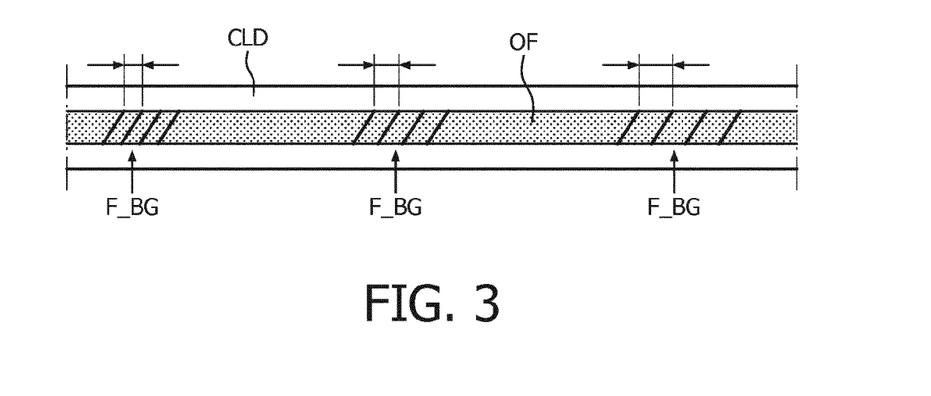
FIG. 3 illustrates a sketch of an embodiment with tilted gratings with unique periods.

FIG. 3 illustrates how the above principle of guiding light out of an optical fiber OF by means of gratings F_BG can be extended to provide position or longitudinal control of where light is guided out of the fiber OF, and thus into adjacently positioned phase change material (not shown in FIG. 3). By varying the grating period along the length of the optical fiber OF (chirped grating), or by having several segments of tilted Bragg gratings F_BG with a unique grating period, the location along the length of the optical fiber OF at which the light is trapped out can be controlled by adapting the wavelength of the light source providing light to the proximal end of the optical fiber OF. The different grating periods of the gratings F_BG is indicated by the lengths of the double arrows which are seen to increase from the one F_BG to the left which has a short grating period, to the one F_BG to the right which has a longer grating period. This allows longitudinal position control of the stiffness of the elongated device by means of varying the wavelength of light applied.

There are several approaches to heat up the phase change material. One way is to adapt the cladding such that it has a high absorption coefficient such that it heats up by the light that is coupled into the cladding. Heat could be transferred by thermal conduction from the cladding to the phase change material. For this, it is essential that there is good thermal contact between the cladding and the phase change material. Another approach is to remove the cladding from the optical fiber such that the light is not coupled into cladding modes but into radiation modes. For this, it is important for a proper effect, that the phase change material surrounding the optical fiber core has a high absorption coefficient such that the light is converted into sensible heat. This could for example be achieved by adding a black absorber (such as black carbon particles) to the PCM.

Figure 4:
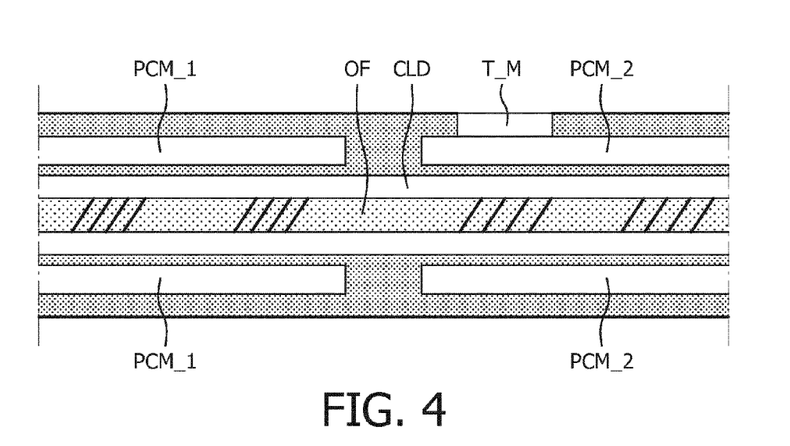
FIG. 4 illustrates a sketch of an embodiment where phase change material is embedded in a tube around the optical fiber.

FIG. 4 illustrates an optical fiber OF arranged in a cladding CLD, which is again arranged within a tube of a tube material T_M, e.g. Pebax® or Pebax® filled with thermal conductive ceramic or metal particles, which has a high thermal conduction effect. Blocks of phase change material PCM_1, PCM_2 is embedded or integrated in the tube material T_M. In the optical fiber OF tilted gratings are indicated at positions corresponding to the longitudinal positions of the blocks of phase change materials PCM_1, PCM_2. These gratings are indicated to have different grating periods, thus allowing selection between activating phase change of PCM_1 and PCM_2 by correspondingly providing light by a matching wavelength.

Figure 5:
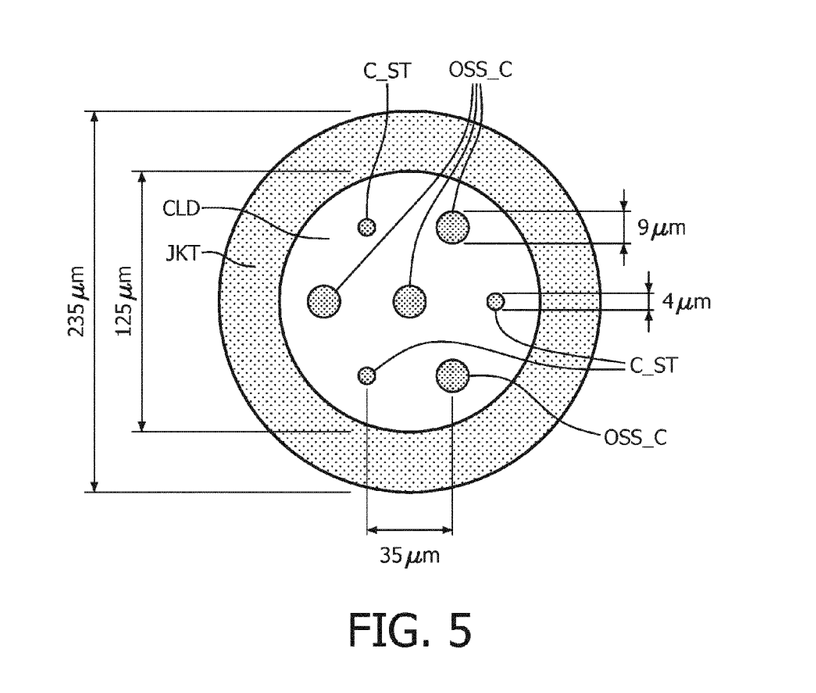
FIG. 5 illustrates a cross-sectional sketch of a multi-core embodiment.

FIG. 5 illustrates a cross-sectional of a specific embodiment with an optical fiber having a plurality of optical fiber cores OSS_C, C_ST arranged within one common cladding CLD and jacket JKT. Especially, such multi-core optical fibers are used in a technique known as Optical Shape Sensing (OSS), where optical interrogation of strain sensing optical elements in the optical fiber core(s) is used to provide reconstruction of the shape of an optical fiber, and thus the shape of an elongated device in which such optical fiber is positioned.

In the illustrated example, stiffening of an elongated device by means of phase change material is combined with OSS for shape sensing. In the shown example, three of the optical fiber cores C_ST are arranged for providing light to phase change material arranged (not shown) outside the jacket JKT of the optical fiber, while four fiber cores OSS_C are arranged for OSS. Such combination of stiffness control and OSS is advantageous for providing a compact (thin) medical interventional instrument. Such instrument allows a user to navigate the instrument by means of the stiffening control feature, and at the same time, navigation is made easy by means of the OSS facility that can allow the user to real-time monitor e.g. the 3D position of the tip of the instrument.

Figure 6:
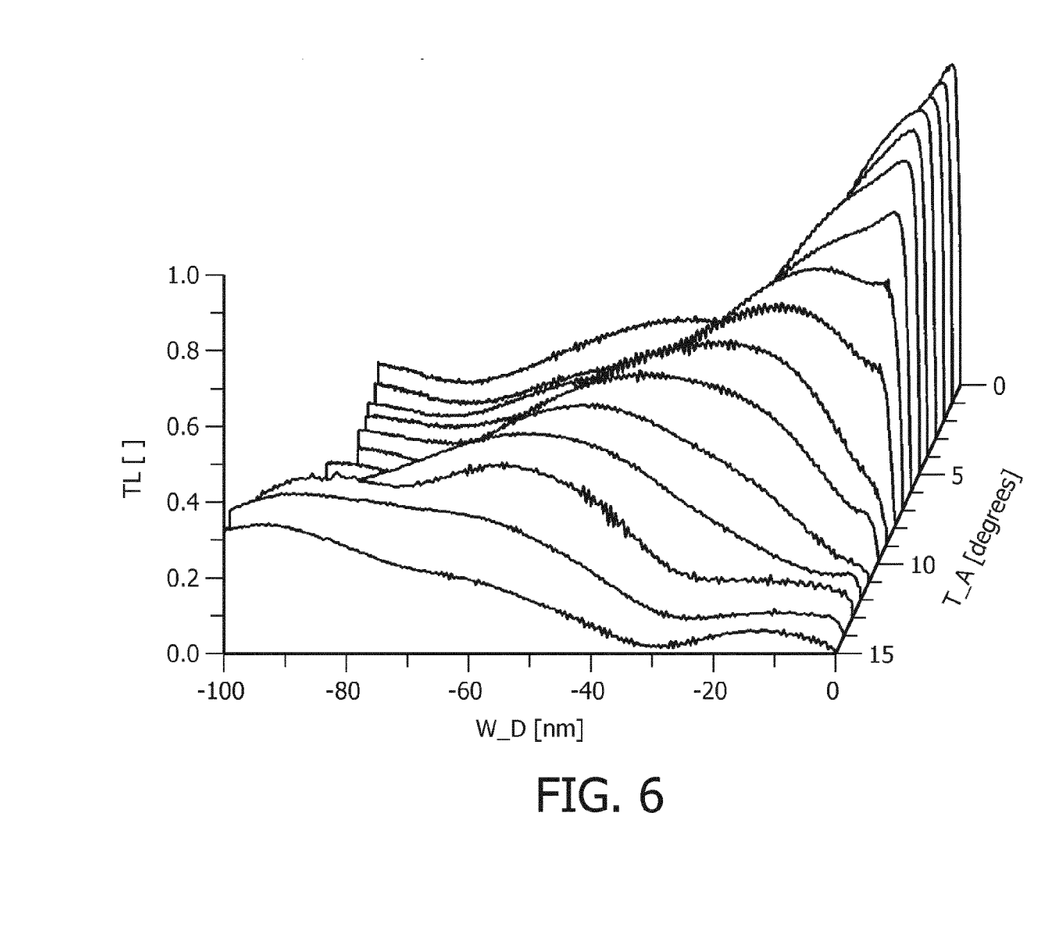
FIG. 6 illustrates a graph showing measured light transmission loss spectra versus grating tilt angle for an optical fiber.

FIG. 6 shows a graph of transmission loss TL experimentally measured for an optical fiber with tilted gratings. The transmission loss TL spectra (wavelength detuning) W_D is shown versus tilt angle T_A (in the angle interval 0°-15°) of the tilted gratings. The bandwidth and the amount of trapped out light depends on the tilt angle T_A of the grating planes, as can be seen. This means that the tilt angle T_A can preferably be chosen in such a way that all light of a specific range of wavelengths (peak wavelength+bandwidth) is evenly distributed along the targeted PCM segment. Also, the difference between the periods of the gratings should be sufficiently large, and hence also the bandwidth of the light source, such that each segment can be addressed individually.

In general, tilt angles in the range of 5° to 45° may be preferred. In general, light within the wavelength range of 400 nm to 2000 nm may be preferred for activating a change of phase in the phase change material.

Figure 7:
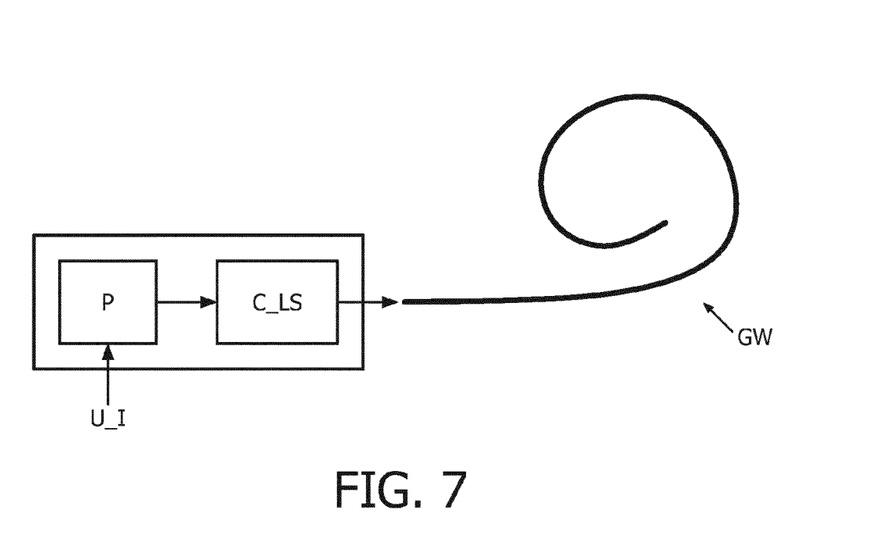
FIG. 7 illustrates a system embodiment.

FIG. 7 shows a simple block diagram of parts of a system embodiment, e.g. a medical system for performing a FEVAR procedure. A guide wire GW comprising an elongated device as explained above including an optical fiber arranged for applying heat to preferably a plurality of different portions of phase change material arranged along the guide wire GW to selectively allow stiffening of the different portions of phase change material the elongated device. A light source C_LS is arranged for connection to the proximal end of optical fiber in the guide wire GW. This light source C_LS serves to provide light to cause the selected portion of phase change material to change its stiffness from one stiffness value to a different stiffness value. The light source C_LS is controlled by a processor P in accordance with a user input U_I. Especially, this user input U_I is obtained from a control device allowing a user to control the stiffness of selected parts of the guide wire to facilitate navigation, e.g. as part of a FEVAR procedure. The processor P executes a control algorithm that translates the user input U_I into e.g. a light wavelength to be applied by the light source C_LS, so as to activate the desired parts of phase change material in the guide wire GW in order to obtain behavior of the guide wire GW according to the user input U_I.

Especially, the guide wire GW may comprise optical fiber cores arranged for application of OSS. In such case, the system may comprise an optical console arranged for optical interrogation of such OSS fiber cores, and accordingly generation of an image of a reconstructed 3D shape of the guide wire GW.

Figure 8:
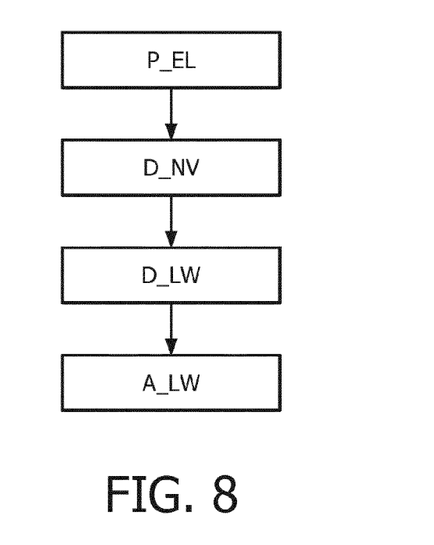
FIG. 8 illustrates steps of a method embodiment.

FIG. 8 shows steps of an embodiment of a method for controlling an elongated device. First step is providing an elongated device P_EL comprising an optical fiber arranged to transmit light from its proximal end to a phase change material arranged along at least a longitudinal portion of the elongated device. Next step is to determine a navigational input D_NV from a user. In response to the user input, e.g. longitudinal position where the user want a stiffening of the elongated device, a step of determining a light wavelength D_LW to be applied to the optical fiber is performed. Finally, a step of providing light A_LW to a proximal end of the optical fiber with the determined wavelength is performed. Hereby, the desired portion of phase change material is optically heated to cause the desired portion of the phase change material to change its stiffness from one stiffness value to a different stiffness value.

To sum up, the invention provides an elongated device, e.g. an interventional guide wire or catheter, comprises an optical fiber OF arranged to allow transmission of light to phase change material PCM arranged long the elongated device, for optically heating the phase change material PCM to change its stiffness from one stiffness value to a different stiffness value. Using distributed tilted or blazed Bragg gratings with light wavelength dependent unique grating periods along the optical fiber, it is possible to provide a guide wire or catheter which can be stiffness controlled at selected longitudinal portions. Especially, it may be preferred to be able to control the behavior of the tip of a guide wire or catheter for optimal navigation, e.g. during a FEVAR procedure. Portions of phase change material PCM_1, PCM_2 arranged inside a tube material T_M can be activated at selected longitudinal parts of the elongated device. In combination with Optical Shape Sensing, an optimal control of a medical interventional instrument can be obtained.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. An elongated device comprising:
   blocks of phase change material arranged at different longitudinal positions of a longitudinal extension of the elongated device; and
   an optical fiber arranged in relation to the phase change material so as to allow transmission of light from a proximal end of the optical fiber to at least part of the phase change material for optically providing heat to said at least part of the phase change material to cause said at least part of the phase change material to change its stiffness from one stiffness value to a different stiffness value,
   wherein the optical fiber comprises a plurality of longitudinal portions with tilted or blazed gratings arranged for guiding light in a direction away from a longitudinal extension of the optical fiber at respective longitudinal portions of the optical fiber, wherein a tilt angle of the gratings is selected so as to guide light of a specific range of wavelengths evenly along at least a longitudinal portion of the optical fiber.

2. The elongated device according to claim 1, wherein the optical fiber is arranged to transmit light from a proximal end of the optical fiber for providing heat to a plurality of different portions of a block of the blocks of phase change material arranged at different longitudinal positions of the elongated device.

3. The elongated device according to claim 1, wherein the tilted or blazed gratings at said plurality of longitudinal portions of the optical fiber are arranged to guide light in a direction away from the longitudinal extension of the optical fiber at respective different wavelengths of light.

4. The elongated device according to claim 3, wherein the phase change material is arranged along at least along said longitudinal portions of the optical fiber, so as to allow wavelength dependent change of stiffness of different longitudinal portions of the elongated device.

5. The elongated device according to claim 1, wherein the gratings at said plurality of longitudinal portions of the optical fiber have respective unique grating periods, so as to allow light wavelength dependent activation of phase change material arranged at said plurality of longitudinal portions.

6. The elongated according to claim 1, wherein said tilted or blazed gratings comprise Bragg gratings.

7. The elongated device according to claim 1, comprising an elongated tube containing said phase change material at least at a part of its longitudinal extension, wherein the optical fiber is arranged inside said elongated tube.

8. The elongated device according to claim 1, wherein phase change material is arranged at least along a distal end portion of the elongated device.

9. The elongated device according to claim 1, wherein the elongated device is an interventional guide wire or an interventional catheter.

10. A system comprising:
   an elongated device comprising:
      blocks of phase change material arranged at different longitudinal positions of a longitudinal extension of the elongated device, and
      an optical fiber arranged in relation to the phase change material so as to allow transmission of light from a proximal end of the optical fiber to at least part of the phase change material for optically providing heat to said at least part of the phase change material to cause said at least part (P) of the phase change material to change its stiffness from one stiffness value to a different stiffness value, wherein the optical fiber comprises a plurality of longitudinal portions with tilted or blazed gratings arranged for guiding light in a direction away from a longitudinal extension of the optical fiber at respective longitudinal portions of the optical fiber, wherein a tilt angle of the gratings is selected so as to guide light of a specific range of wavelengths evenly along at least a longitudinal portion of the optical fiber; and
   a light source arranged for connection to the proximal end of optical fiber for providing light to cause said at least part of the phase change material to change its stiffness from one stiffness value to a different stiffness value.

11. A method for controlling an elongated device, the method comprising act of:
   providing an elongated device comprising an optical fiber arranged to transmit light from its proximal end to blocks of phase change material arranged along different longitudinal portions of the elongated device, wherein the optical fiber comprises a plurality of longitudinal portions with tilted or blazed gratings arranged for guiding light in a direction away from a longitudinal extension of the optical fiber at respective longitudinal portions of the optical fiber, wherein a tilt angle of the gratings is selected so as to guide light of a specific range of wavelengths evenly along at least a longitudinal portion of the optical fiber; and
   providing light to a proximal end of the optical fiber, so as to optically provide heat to said portion of the phase change material to cause said portion of the phase change material to change its stiffness from one stiffness value to a different stiffness value.

* * * * *